US009858892B2

(12) United States Patent
Rezaee

(10) Patent No.: US 9,858,892 B2
(45) Date of Patent: Jan. 2, 2018

(54) METHOD AND COMPUTING DEVICE FOR IDENTIFYING A PIXEL VISIBILITY LOSS CONDITION

(71) Applicant: Change Healthcare LLC, Alpharetta, GA (US)

(72) Inventor: Mahmoud Ramze Rezaee, North Vancouver (CA)

(73) Assignee: CHANGE HEALTHCARE LLC, Alpharetta, GA (US)

( * ) Notice: Subject to any disclaimer, the term of this patent is extended or adjusted under 35 U.S.C. 154(b) by 255 days.

(21) Appl. No.: 14/229,331

(22) Filed: Mar. 28, 2014

(65) Prior Publication Data

US 2015/0279323 A1 Oct. 1, 2015

(51) Int. Cl.
*G09G 5/10* (2006.01)
*G06F 19/00* (2011.01)
*G09G 5/00* (2006.01)

(52) U.S. Cl.
CPC .............. *G09G 5/10* (2013.01); *G06F 19/321* (2013.01); *G09G 5/00* (2013.01); *G09G 2320/0271* (2013.01); *G09G 2320/0606* (2013.01); *G09G 2320/0673* (2013.01); *G09G 2340/14* (2013.01); *G09G 2360/16* (2013.01); *G09G 2380/08* (2013.01)

(58) Field of Classification Search
None
See application file for complete search history.

(56) References Cited

U.S. PATENT DOCUMENTS

| 2007/0008560 | A1* | 1/2007 | Eschbach | H04N 1/6011 358/1.9 |
| 2008/0137948 | A1* | 6/2008 | Tamagawa | H04N 1/6058 382/167 |
| 2009/0060367 | A1* | 3/2009 | Wei | G06T 5/20 382/260 |
| 2011/0181787 | A1* | 7/2011 | Wang | H04N 5/202 348/673 |
| 2012/0154355 | A1* | 6/2012 | Kawai | G09G 3/2007 345/207 |
| 2015/0146997 | A1* | 5/2015 | Li | G06T 5/007 382/274 |

OTHER PUBLICATIONS

"Color Luminance". WorkWithColor.com. http://www.workwithcolor.com/color-luminance-2233.htm. Accessed on Sep. 23, 2016.*

* cited by examiner

*Primary Examiner* — Aaron M Richer
(74) *Attorney, Agent, or Firm* — Alston & Bird LLP

(57) ABSTRACT

A method, a computing device and a computer program product are provided to identify an instance in which a pixel visibility loss condition exists following window leveling. In the context of a method, window and level values and corresponding minimum and maximum values for a window are identified. The method then determines whether the pixel visibility loss condition exists based upon one or more of the window and level values, the minimum value or the maximum value. In this regard, the method determines whether a pixel visibility loss condition exists by determining whether there is a gray scale loss, a gray scale compression or a lack of perceptible distinctiveness between pixels within the window. In an instance in which the pixel visibility loss condition exists, the method causes an indication to be provided to a user.

20 Claims, 8 Drawing Sheets

METHOD AND COMPUTING DEVICE FOR IDENTIFYING A PIXEL VISIBILITY LOSS CONDITION

TECHNOLOGICAL FIELD

An example embodiment of the present invention relates generally to window leveling and, more particularly, to identifying an instance in which a pixel visibility loss condition exists following window leveling.

BACKGROUND

Medical images are captured by a wide variety of modalities including, for example, computerized tomography (CT), magnetic resonance imaging (MRI), computed radiography (CR), digital radiography (DR) and mammography (MG). Regardless of the modality, the medical images are comprised of a plurality of pixels, each of which has a respective pixel value. Once visualized, each pixel value corresponds to a distinct gray level or a distinct shade of color, such as red, green or blue depending upon the respective color channel. Many modalities, such as each of the foregoing examples, have pixels with a relatively large range of values, thereby defining a dynamic pixel value range. In this regard, the range of pixel values may be substantially greater than the 256 display values that most displays are capable of presenting. For example, depending upon whether the image is an original image or has been post-processed, the pixel range of an image could be expressed by 10 bits so as to have 1024 different pixel values, 12 bits so as to have 4096 different pixel values or 16 bits so as to have 65536 different pixel values.

Most displays and most operating systems that support the display of medical images only allow for 256 shades of gray (in an instance in which a grey scale monitor is utilized) or 256 shades of each of red, green and blue colors (in an instance in which a color monitor having red, green and blue color channels is utilized) to be simultaneously displayed. Due to the differences between the dynamic pixel value range and the number of different display values that may be simultaneously presented by a display, the dynamic pixel value range may be divided into intervals, each of which has an equal number of different values, e.g., 256 different pixel values, as those which can be simultaneously presented by display. Within the interval of pixel values, the different pixel values are represented by different shades of gray or different shades of color. For pixel values that are below the minimum pixel value of the interval, the pixel values may be mapped to the minimum display value of the interval. Similarly, for pixel values that are above the maximum pixel value of the interval, the pixel values may be mapped to the maximum display value of the interval.

A user may modify the interval across the full dynamic pixel value range so as to permit the user to view the other pixel values. The interval may be defined in terms of a window and a level. The width of the interval in terms of the range of pixel values is termed a window with the center of the range of pixel values within the window being termed the level. In general, a window may be of any size with the windowing process mapping the pixel value range of the window from [center−width/2, center+width/2] to the nearest integer [0-255] for a display capable of presenting 256 shades. The mapping of the pixel values to the display intensities may be performed in accordance with a function. Depending on the type of function, a group of pixels may map to some grayscale (or color) values or some grayscale (or color) values may not be used at all.

This mapping of pixel values and output intensities is generally termed window leveling. In many modalities, the optimal window level is not known in advance and users must manually modify the window level until a proper value is found. This modification of the window level may be performed by user interaction with an image viewer application, such as a Picture Archiving and Communication System (PACS) viewer, through an input device, such as a mouse. In this regard, a user may modify the window level by moving the window throughout the dynamic pixel value range so as to permit different pixel values to be displayed. In an instance in which the dynamic pixel value range exceeds the number of different pixel values that may be simultaneously presented by a display, some of the pixel values of the input image will not be accurately represented by the image presented by the display regardless of the window leveling. Indeed, pixel values of the input images that fall outside the window may be represented or rather, mis-represented, by a pixel value within the window. A user viewing the image presented by the display may not recognize the modification of the pixel values and, as a result, may not realize that the visual representation of the input image does not entirely accurately reflect the input image.

BRIEF SUMMARY

A method, a computing device and a computer program product are provided in accordance with an example embodiment in order to identify an instance in which a pixel visibility loss condition exists following window leveling, such as an instance in which a pixel value of an input images that falls outside a window is modified so as to be represented by a pixel value within the window. Based upon the identification of a pixel visibility loss condition, the method, computing device and a computer program product of an example embodiment may notify a user so that the user is put on notice that the input image has been modified. As such, a user can take into account the modification of the input image in analyzing the image that is presented, such as by a display.

In an example embodiment, a method is provided that includes identifying window and level values and corresponding minimum and maximum values for a window. The method of this example embodiment also includes determining whether a pixel visibility loss condition exists based upon one or more of the window and level values, the minimum value or the maximum value. In this regard, the method may determine whether a pixel visibility loss condition exists by determining whether there is one or more of a gray scale loss, a gray scale compression or a lack of perceptible distinctiveness between pixels within the window. In an instance in which the pixel visibility loss condition exists, the method of this example embodiment also includes causing an indication to be provided to a user, such as by causing a visible indication to be provided via the display.

The method of an example embodiment may determine whether there is a gray scale loss by determining that there is a gray scale loss in an instance in which one or more gray scale values in an input image are not assigned to any pixel value to be presented by a display. In an example embodiment, the method may determine whether there is a gray scale compression by determining that there is a gray scale compression in an instance in which a single display value to be presented by the display is assigned to two or more pixel values, such as two or more consecutive pixel values, within the window. The method of an example embodiment may determine whether there is a lack of perceptible distinctiveness between pixels within the window by determining whether there is a lack of perceptible distinctiveness between pixels within the window based upon a luminance range of the display and just noticeable indices.

In another example embodiment, a computing device is provided that includes processing circuitry configured to identify window and level values and corresponding minimum and maximum values for a window. The processing circuitry of this example embodiment is also configured to determine whether a pixel visibility loss condition exists based upon one or more of the window and level values, the minimum value or the maximum value. In this regard, the processing circuitry may be configured to determine whether a pixel visibility loss condition exists by determining whether there is one or more of a gray scale loss, a gray scale compression or a lack of perceptible distinctiveness between pixels within the window. In an instance in which the pixel visibility loss condition exists, the processing circuitry of this example embodiment is also configured to cause an indication to be provided to a user, such as by causing a visible indication to be provided via the display.

The processing circuitry of an example embodiment may be configured to determine whether there is a gray scale loss by determining that there is a gray scale loss in an instance in which one or more gray scale values in an input image are not assigned to any pixel value to be presented by a display. In an example embodiment, the processing circuitry may be configured to determine whether there is a gray scale compression by determining that there is a gray scale compression in an instance in which a single display value to be presented by the display is assigned to two or more pixel values, such as two or more consecutive pixel values, within the window. The processing circuitry of an example embodiment may be configured to determine whether there is a lack of perceptible distinctiveness between pixels within the window by determining whether there is a lack of perceptible distinctiveness between pixels within the window based upon a luminance range of the display and just noticeable indices.

In a further example embodiment, a method is provided that includes identifying each distinct pixel value of an input image and associating a respective pixel visibility flag with each distinct pixel value. Based upon window and level values and corresponding minimum and maximum values for a window boundary of a display, the method of this example embodiment determines whether there is a gray scale loss, a gray scale compression or a lack of perceptible distinctiveness between pixels within the window. In an instance in which there is no gray scale loss, no gray scale compression and no lack of perceptible distinctiveness between pixels within the window, the method of this example embodiment sets the pixel visibility flag associated with each pixel value within the window. In an instance in which not all pixel visibility flags for the pixel values of the input image have been set, the method of this example embodiment causes an indication to be provided to a user, such as by causing a visible indication to be provided via the display.

The method of an example embodiment may determine whether there is a gray scale compression by determining that there is a gray scale compression in an instance in which a single display value to be presented by the display is assigned to two or more pixel values, such as two or more consecutive pixel values, within the window. In an example embodiment, the method may determine whether there is a lack of perceptible distinctiveness between pixels within the window by determining whether there is a lack of perceptible distinctiveness between pixels within the window based upon a luminance range of the display and just noticeable indices. The method of an example embodiment may also include initially causing the visible indication to be provided prior to determining whether there is a gray scale compression or a lack of perceptible distinctiveness between pixels within the window. In this embodiment, the method may cause the visible indication to be provided to the user by eliminating the visible indication in the instance in which all pixel visibility flags for the pixel values of the input image have been set.

In yet another example embodiment, a computing device is provided that includes a processing circuitry configured to identify each distinct pixel value of an input image and to associate a respective pixel visibility flag with each distinct pixel value. Based upon window and level values and corresponding minimum and maximum values for a window boundary of a display, the processing circuitry of this example embodiment is configured to determine whether there is a gray scale loss, a gray scale compression or a lack of perceptible distinctiveness between pixels within the window. In an instance in which there is no gray scale loss, no gray scale compression and no lack of perceptible distinctiveness between pixels within the window, the processing circuitry of this example embodiment is configured to set the pixel visibility flag associated with each pixel value within the window. In an instance in which not all pixel visibility flags for the pixel values of the input image have been set, the processing circuitry of this example embodiment is configured to cause an indication to be provided to a user, such as by causing a visible indication to be provided via the display.

The processing circuitry of an example embodiment may be configured to determine whether there is a gray scale compression by determining that there is a gray scale compression in an instance in which a single display value to be presented by the display is assigned to two or more pixel values, such as two or more consecutive pixel values, within the window. In an example embodiment, the processing circuitry may be configured to determine whether there is a lack of perceptible distinctiveness between pixels within the window by determining whether there is a lack of perceptible distinctiveness between pixels within the window based upon a luminance range of the display and just noticeable indices. The processing circuitry of an example embodiment may also be configured to initially cause the visible indication to be provided prior to determining whether there is a gray scale compression or a lack of perceptible distinctiveness between pixels within the window. In this embodiment, the processing circuitry may be configured to cause the visible indication to be provided to the user by eliminating the visible indication in the instance in which all pixel visibility flags for the pixel values of the input image have been set.

BRIEF DESCRIPTION OF THE DRAWINGS

Figure 1:
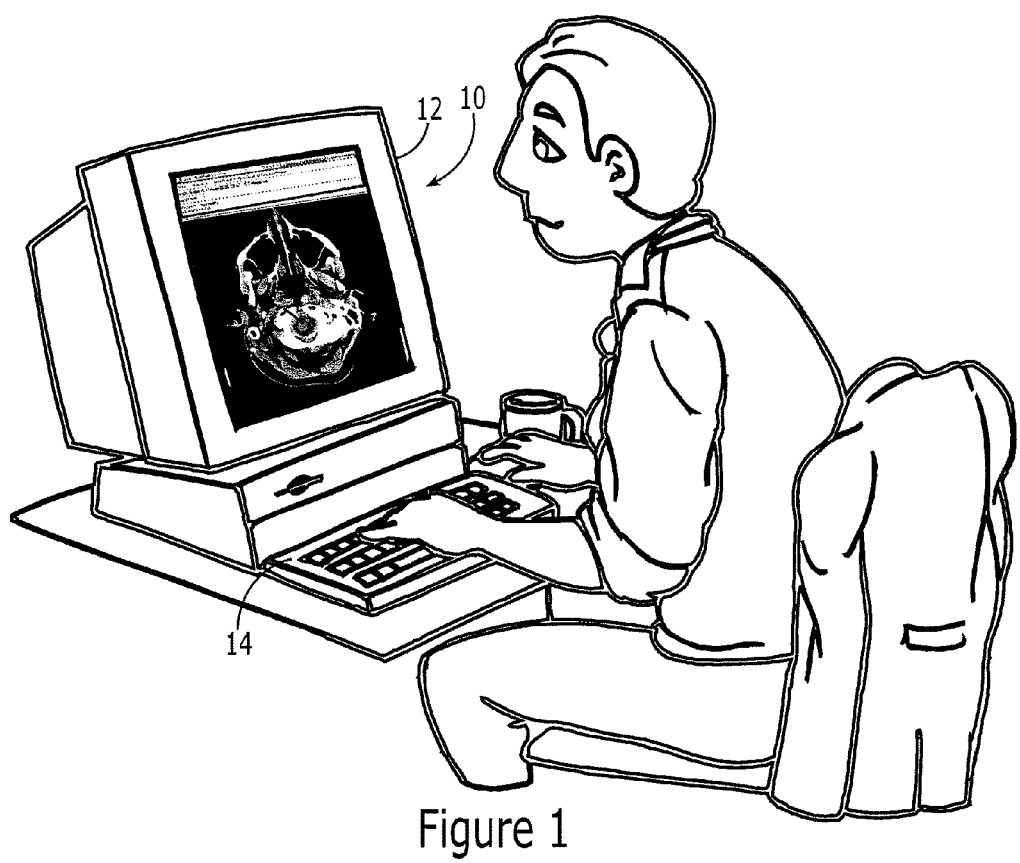
Figure 2:
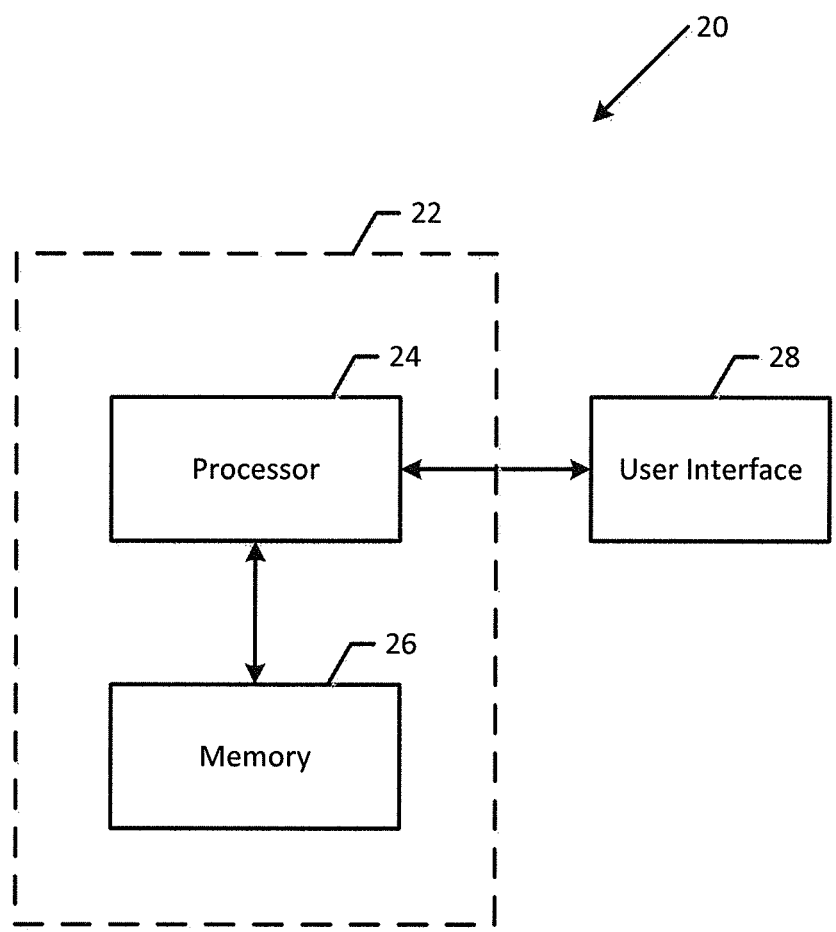
Figure 3:
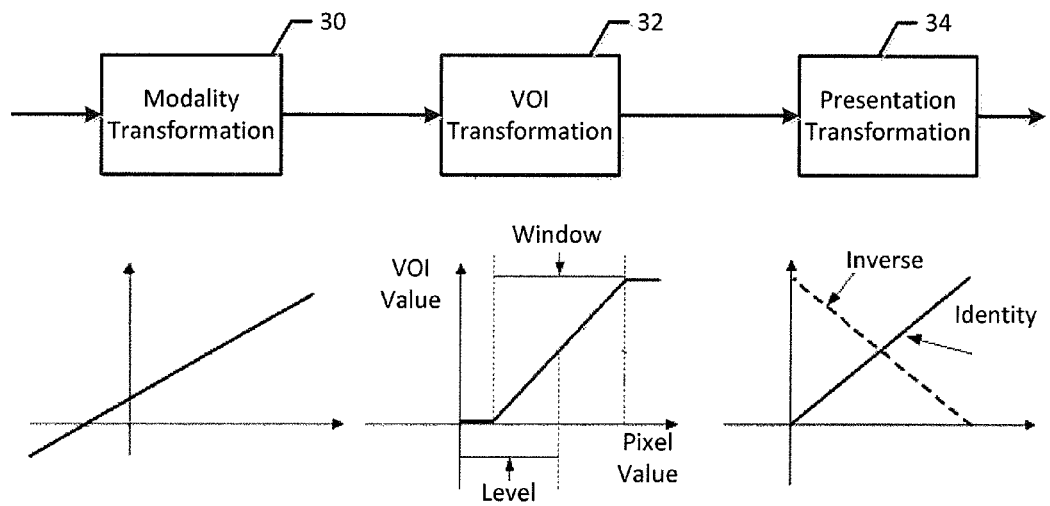
Figure 4:
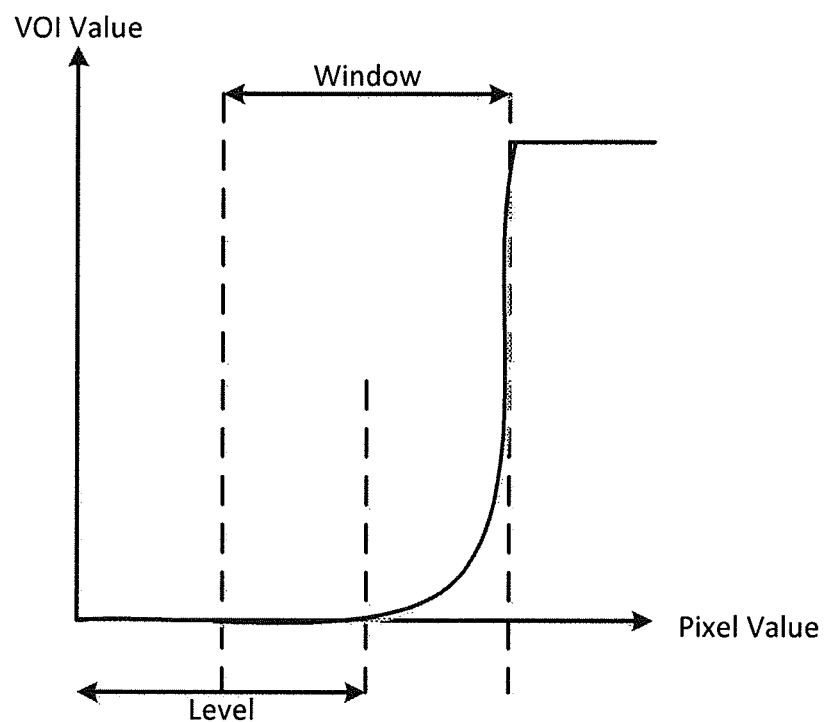
Figure 5A:
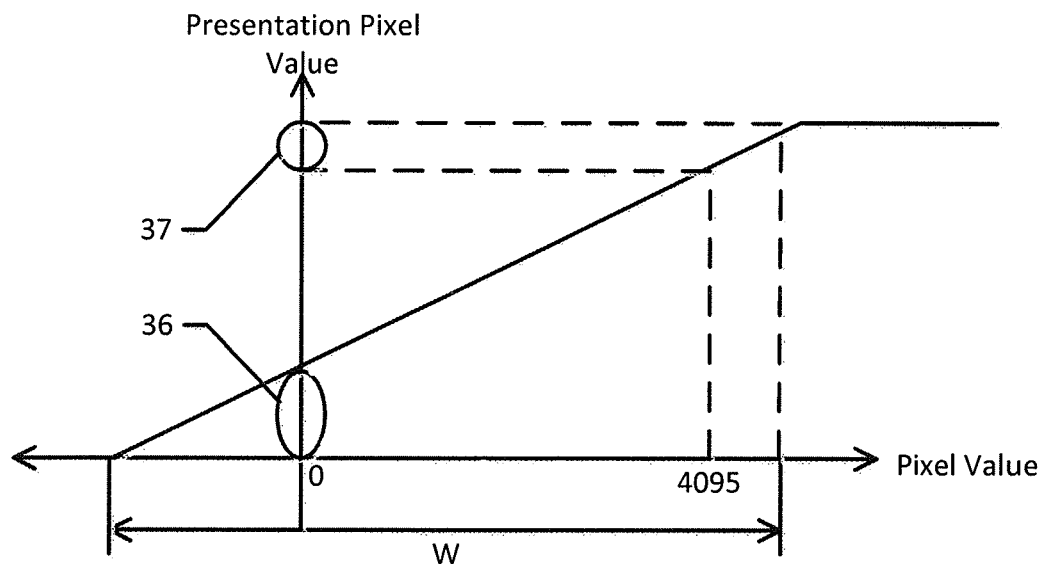
Figure 5B:
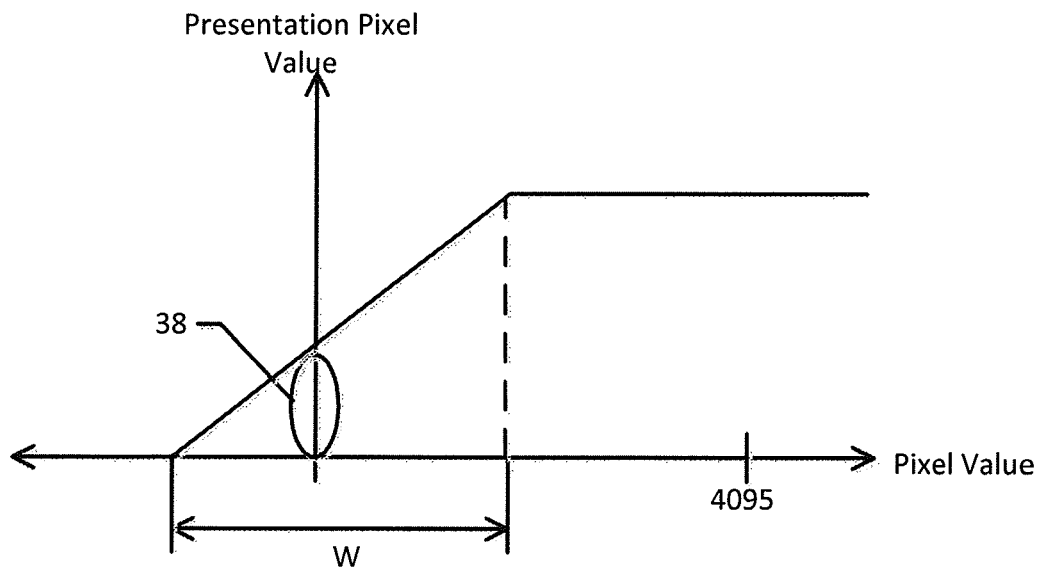
Figure 5C:
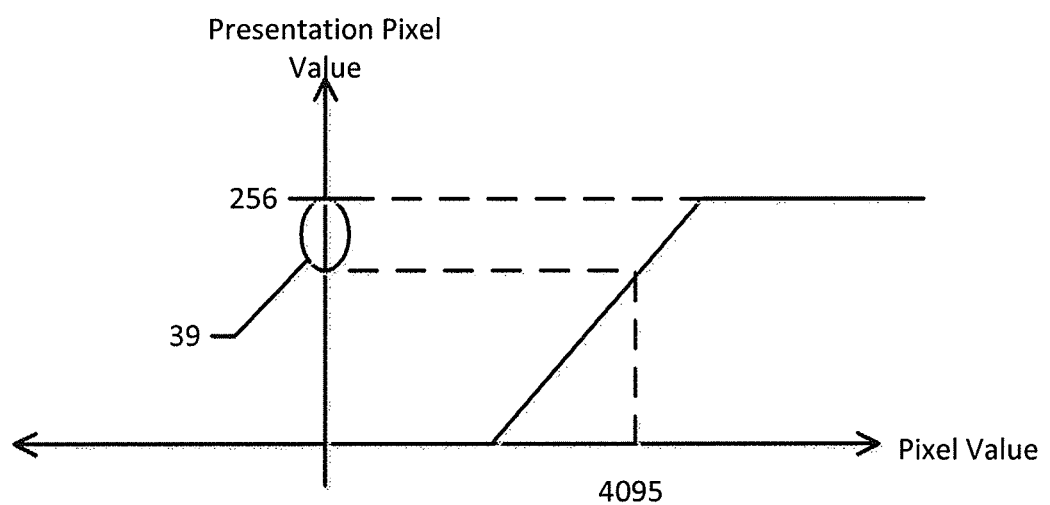
Figure 6:
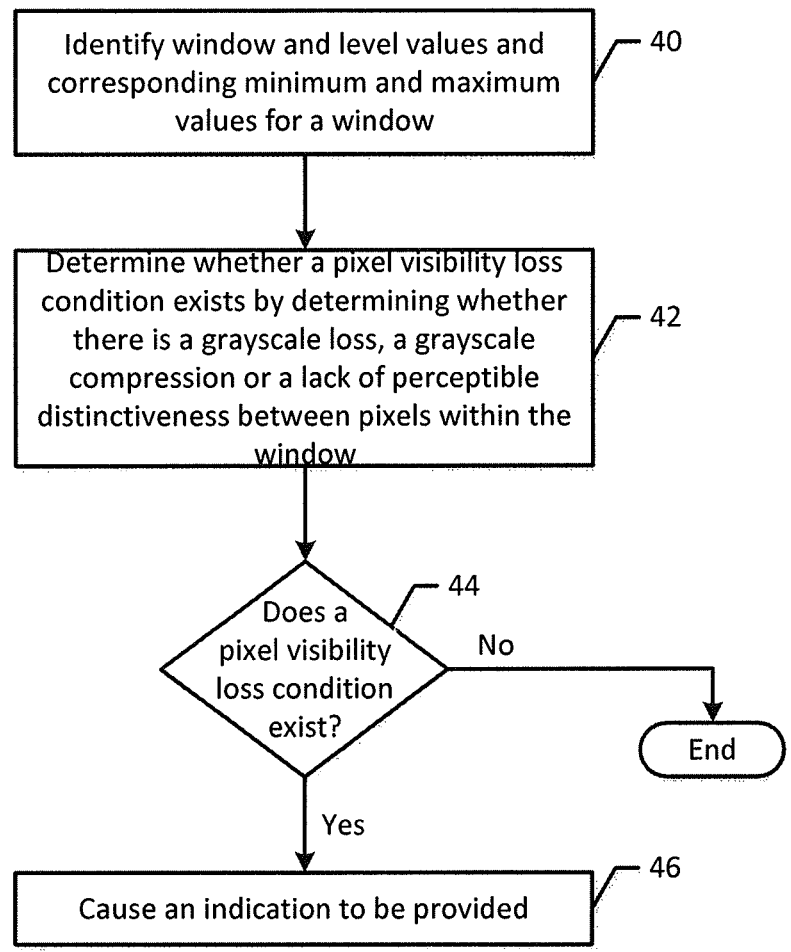
Figure 7:
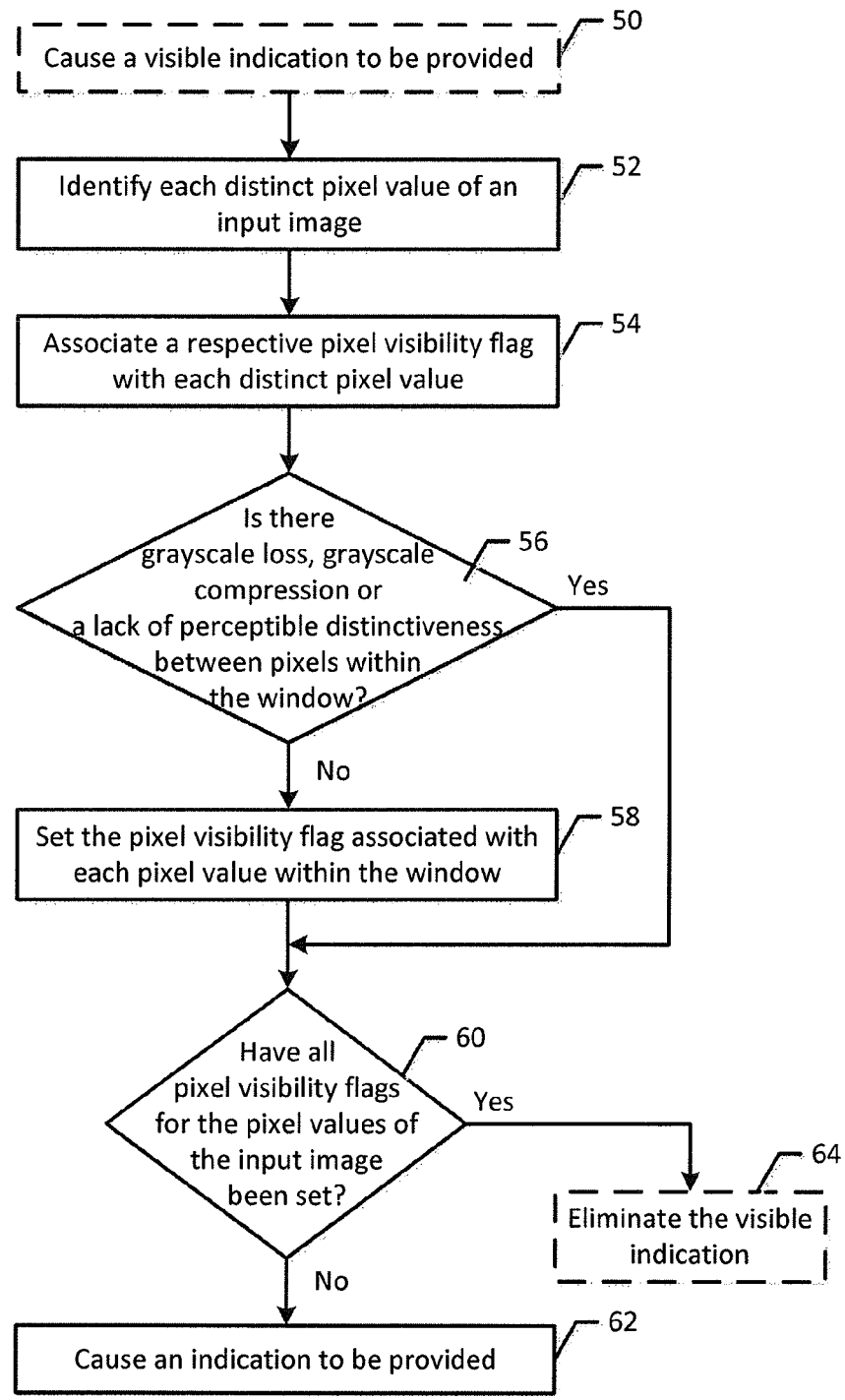

Having thus described example embodiments of the present disclosure in general terms, reference will now be made to the accompanying drawings, which are not necessarily drawn to scale, and wherein:

FIG. 1 is a perspective view of a user viewing an image upon a display;

FIG. 2 is a block diagram of a computing device that may be specifically configured in accordance with an example embodiment of the present invention;

FIG. 3 is a flow diagram and associated graphical representation of the different types of transformations performed upon an image prior to presentation upon a display;

FIG. 4 is a graphical representation of a non-linear transformation function;

FIGS. 5A-5C are graphical representations of different instances in which some portion of the pixel values of the input image is unable to be represented by the display;

FIG. 6 is a flow chart illustrating operations performed, such as by the computing device of FIG. 2, in accordance with an example embodiment of the present invention; and FIG. 7 is a flow chart illustrating operations performed, such as by the computing device of FIG. 2, in accordance with another example embodiment of the present invention.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information" and similar terms may be used interchangeably to refer to data capable of being transmitted, received and/or stored in accordance with embodiments of the present invention. Thus, use of any such terms should not be taken to limit the spirit and scope of embodiments of the present invention.

A method, computing device and computer program product are provided according to example embodiments of the present invention in order to identify an instance in which a pixel visibility loss condition exists following window leveling, such as an instance in which the assigned display value of pixel values of an input image that falls outside a window are similar to the display value of a different pixel is modified so as to be represented by a pixel value within the window. As a result of this assignment of the same display value for pixels with different values, many pixels of the input image are no longer accurately represented, that is, no longer distinguishable, thereby resulting in pixel visibility loss. Based upon the identification of a pixel visibility loss condition, the method, computing device and a computer program product of an example embodiment may notify a user such that the user is effectively notified of the modification of the input image. The user may therefore take into account the representation of the input image during their analysis of the image that is presented, such as by a display.

A pixel visibility loss condition in which a pixel value of an input image is not uniquely and distinctly represented by the image presented by a display may be identified by the method, computing device and computer program product in a variety of settings and in conjunction with a variety of different types of images. In an example embodiment depicted in FIG. 1, a user may interact with a computing device 10, such as a workstation, a personal computer, an image viewing station, e.g., a PACS station, a tablet computer, a laptop computer or a mobile terminal, e.g., a smartphone, a personal digital assistant (PDA) or the like.

Regardless of the manner in which the computing device is instantiated, the computing device may include a display 12 and a keyboard 14 or other type of user interface. As shown in FIG. 1, an image may be presented upon the display. In an example embodiment, the image may be a medical image, such as a medical image captured by any of a wide variety of different modalities, such as CT, MRI, CR, DR or MG modalities. In one embodiment, a radiologist may review the images. However, other types of users, such as other health care practitioners, patients or the like, may view the images. As described below, the identification of the pixel visibility loss condition may permit the user to be notified, thereby informing the user's subsequent review of the resulting image.

As shown in FIG. 2, an example embodiment of a computing device 20 that may be specifically configured in accordance with an example embodiment of the present invention is depicted. The computing device of FIG. 2 may be the same computing device that provides for the display of images as shown in FIG. 1. Alternatively, the computing device of FIG. 2 may be distinct from the computing device 10 that provides for the display of the images, but may be in communication therewith so as to identify a pixel visibility loss condition and to notify the user. As such, the computing device in FIG. 2 may be embodied by PACS workstation, a computer workstation, a personal computer, a tablet computer, a laptop computer, a mobile terminal, such as a smartphone, a PDA or the like. Alternatively, the computing device 20 may be a server or other network-based computing device that interacts with a computer device 10 that presents images upon the display in order to perform certain functionalities, such as to identify a pixel visibility loss condition.

Regardless of the manner in which the computing device 20 is embodied, the computing device may include of one embodiment may be generally depicted as shown in FIG. 2 so as to include or to be associated and in communication with processing circuitry 22 that is configurable to perform functions in accordance with one or more example embodiments disclosed herein. In this regard, the processing circuitry may be configured to perform and/or control performance of one or more functionalities of the computing device in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 22 may include a processor 24 and, in some embodiments, such as that illustrated in FIG. 2, may further include memory 26. The processing circuitry may be in communication with or otherwise control a user interface 28, such as a display 12, a keyboard 14 and/or other input/output mechanisms and, in some embodiments, may also optionally include a communication interface for communicating with other computing systems. As such, the processing circuitry may be embodied as a circuit chip (e.g., an integrated circuit chip) configured (e.g., with hardware, software or a combination of hardware and software) to perform operations described herein.

The processor 24 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device 20 as described herein. The plurality of processors may be embodied on a single computing device or distributed across a plurality of computing devices collectively configured to function as the computing device. In some example embodiments, the processor may be configured to execute instructions stored in the memory 26 or otherwise accessible to the processor. As such, whether configured by hardware or by a combination of hardware and software, the processor may represent an entity (e.g., physically embodied in circuitry—in the form of processing circuitry 22) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 26 may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computing device 20. The memory may be configured to store information, data, applications, instructions and/or the like for enabling the computing device to carry out various functions in accordance with one or more example embodiments. For example, the memory may be configured to buffer input data for processing by the processor 24. Additionally or alternatively, the memory may be configured to store instructions for execution by the processor. As yet another alternative, the memory may include one or more databases that may store a variety of files, contents or data sets, such as medical images, e.g., image studies, for a plurality of patients. Among the contents of the memory, applications may be stored for execution by the processor in order to carry out the functionality associated with each respective application. In some cases, the memory may be in communication with one or more of the processor or the user interface 28 via a bus or buses for passing information among components of the computing device.

Having now described a computing device 20 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

An input image oftentimes undergoes one or more transformations in order to transform the pixel values of the input image into corresponding pixel values, hereinafter referenced as presentation pixel values, of the image that is presented upon the display 12. By way of example, the Digital Imaging and Communications in Medicine (DICOM) standard defines a series of transformations that medical images undergo prior to presentation. As shown in block 30 of FIG. 3, the input image may initially undergo a modality transformation. The modality transformation transforms manufacturer dependent pixel values of the input image into corresponding pixel values that are manufacturer independent. Various predefined types of modality transformations may be utilized including, for example, a Hounsfield unit conversion for CT images and an optical density transformation for an input image provided by a film digitizer. The modality transformation is typically applied by the viewing application and is not available to be modified by a user. An input image and pixel values of the input image will be referenced hereinafter. The input image and the pixel values of the input image may relate to the input image prior to being subjected to the modality transformation or may relate to the image following the modality transformation in an instance in which a modality transformation is applied.

Following the modality transformation, the DICOM standard subjects the image with manufacturer independent pixel values to a value of interest (VOI) transformation. See block 32 of FIG. 3. The VOI transformation is configured to transform the manufacturer independent pixel values into corresponding pixel values that are meaningful for presentation. As shown in FIG. 3, the VOI transformation may define a window of pixel values having a width (in pixels) of W. A level L may also be defined to be the midpoint of the window. For manufacturer independent pixel values that are less than the minimum value of the window, the pixel values may be set to the minimum pixel value within the window, such as 0. Conversely, for manufacturer independent pixel values greater than the maximum value of the window, the pixel values may be set to the maximum value within the window. Unfortunately, the modification of the pixel values that fall outside the window results in a loss of image quality. Within the window, the VOI transformation may define a function, such as a linear function as shown in FIG. 3 or any of a variety of non-linear functions as shown, for example, in FIG. 4, that defines the relationship between the manufacturer independent pixel values and the VOI pixel values that are more meaningful for presentation upon the display 12. The output of the VOI transformation may be either scaled to the full range of the display in an instance in which there is no subsequent transformation, such as no subsequent presentation transformation, or scaled to the full input range of the subsequent transformation, such as the presentation transformation, to permit the subsequent transformation to, in turn, generate an output spanning the full range of the display.

For a window having a level L and a width W, the relationship between the manufacturer independent pixel values x provided by the modality transformation and the VOI pixel values y that range from $y_{min}$ to $y_{max}$ may be defined by pseudo-code as follows:

```
if (x <= L - 0.5 - (W-1)/2), then y = y_min
else if (x > L - 0.5 + (W-1)/2), then y = y_max,
else y = ((x - (L - 0.5)) / (W-1) + 0.5) * (y_max - y_min)+ y_min
```

As the foregoing pseudo-code indicates, the range of the pixel values of the input image, as represented by the manufacturer independent pixel values, may exceed the window that defines the range of VOI values for the pixels to be presented upon the display 12. Thus, the VOI transformation may effectively compress the contrast range of the image into a narrower band and serve to flatten the appearance of the image.

As shown in block 34 of FIG. 3, the DICOM standard may also define a presentation transform. The presentation transform may be an identity transform as shown in a solid line in FIG. 3 or an inverse function as shown in a dashed line that changes the polarity of the display, such that a black pixel becomes a white pixel, a white pixel becomes a black pixel and so on. The result of the presentation transform are presentation pixel values, e.g., P-values, that may be provided to the display 12 which, in turn, will produce a range of luminance, such as in accordance with the DICOM grayscale display function, in response thereto.

In addition to the loss that may occur due to the modification of pixel values of the input image that fall outside the window, an additional loss may occur in an instance in which the window utilized during the VOI transformation is larger than the range of pixel values that may be distinctly presented by the display 12. For example, the window may include 1024 pixel values, while the display may only be capable of presenting 256 distinct pixel values. In this instance, the VOI transformation will be bijective in that different pixel values of the input image will be converted to the same presentation pixel value such that the different pixel values of the input image will not be distinguishable within the resulting image presented by the display. As an example, in an instance in which the window includes 4095 different pixel values and the level is 2048, the presentation transform is the identity function and the display is capable of uniquely presenting 256 different pixel values, every 16 consecutive pixel values of the input image will be converted into a single display pixel value. For example, a first group of pixel values 0, 1, 2, . . . 15 will be converted to a presentation pixel value of 0, a second group of pixel values 16, 17, 18, . . . 31 will be converted to a presentation pixel value of 1 and so on until the final group of pixel values 4080, 4081, . . . 4095 will be converted to a presentation pixel value of 255. Since only one presentation pixel value will represent each 16 consecutive pixel values of the input image, the final luminance generated by the display corresponding to pixels within each group will be the same. In other words, the different pixel values of the pixels within each group from the input image will not be perceptually distinguishable.

In an effort to visually distinguish the input pixel values, the size of the window may be reduced, such as by ¼, and then the window may be moved across all pixel values. However, this approach requires more skill and effort by the user. And while each pixel value of the input image may be individually viewed by moving the window, the full range of pixel values of the input image is not concurrently viewable at any one time.

The DICOM standard does not impose limits on the maximum value of the width of the window or the minimum and/or maximum value of the window, either or both of which may exceed the actual or possible range of input pixel values and result in additional losses in image quality. As shown in FIG. 5A, for example, the window may have the width that exceeds the range of input pixel values, such as pixel values that range from 0 to 4095. In this example, the window is sized to include both negative pixel values and pixel values in excess of 4095, none of which will be included in the input image. Thus, the width of the window results in ranges of presentation pixel values 36 and 37 that will not be utilized as there will be no corresponding input pixel values.

As another example, FIG. 5B depicts a smaller window that also includes negative pixel values. As described above in conjunction with the example of FIG. 5A, the input image will not include the negative pixel values and, as such, a portion 38 of the presentation pixel values will not be utilized as there will be no corresponding negative pixel values within the input image. Because of the smaller width of the window, a number of the input pixel values will exceed the maximum pixel value within the window and, as such, be mapped to the maximum pixel value within the window, thereby effectively compressing the contrast range of the image and flattening the appearance of the image. Another example is depicted in FIG. 5C in which the minimum and maximum values of the window are established such that the minimum value of the window falls within the range of pixel values of the input image and the maximum value of the window falls outside of the range of pixel values of the input image. Thus, the larger pixel values within the window will not correspond to pixel values of the input image, thereby resulting in a region 39 of presentation pixel value that will not be utilized. Additionally, a number of the smaller pixel values of the input image will fall below the minimum pixel value of the window and, as a result, be mapped to the minimum pixel value within the window, thereby effectively compressing the contrast range of the image and flattening the appearance of the resulting image. As the foregoing examples demonstrate, there can be numerous instances in which pixel values of the input image are not accurately and distinctly represented by the image presented by the display 12, thereby resulting in a pixel visibility loss condition.

Referring now to FIG. 6, the operations performed, such as by the computing device 20 of FIG. 2, in order to identify an instance in which a pixel visibility loss condition exists are provided. As shown in block 40 of FIG. 6, the computing device, such as the processing circuitry 22, the processor 24 or the like, may be configured to identify window and level values and corresponding minimum and maximum values for a window. The window and level values and the corresponding minimum and maximum values for the window may be identified based upon input provided by a user, such as via the user interface 28. Alternatively, the window and level values and the corresponding minimum and maximum values for the window may be stored in memory 26 or may be provided by another application.

As shown in block 42 of FIG. 6, the computing device 20, such as the processing circuitry 22, the processor 24 or the like, may be configured to determine whether a pixel visibility loss condition exists based upon one or more of the window and level values, the minimum value of the window or the maximum value of the window. The computing device, such as the processing circuitry, the processor or the like, may be configured to determine whether any one of a variety of different pixel visibility loss conditions exists. As described below, examples of pixel visibility loss conditions include a grayscale loss, a grayscale compression or a lack of perceptible distinctiveness between pixels within the window. Thus, the computing device, such as the processing circuitry, the processor or the like, may be configured to determine whether a pixel visibility loss condition exists by determining whether there is one or more of a grayscale loss, a grayscale compression or a lack of perceptible distinctiveness between pixels within the window.

A grayscale loss occurs in an instance in which one or more grayscale values, that is, pixel values, of an input image are not assigned to any pixel value to be presented by the display. As such, the computing device 20, such as the processing circuitry 22, the processor 24 or the like, may be configured to determine whether there is a grayscale loss by determining that there are one or more grayscale values, i.e., pixel values, of an input image that are not assigned to a pixel value within the window.

Grayscale compression occurs in an instance in which a single display value to be presented by the display is assigned to two or more pixel values within a window. For example, grayscale compression occurs in an instance in which input pixel values that are less than the minimum pixel value within the window are mapped to the minimum pixel value within the window. Similarly, grayscale compression occurs in an instance in which input pixel values that exceed the maximum pixel value within the window are mapped to the maximum pixel value within the window. As another example, grayscale compression occurs in which multiple input pixel values are mapped to the same presentation pixel value, such as in an instance in which the window is larger than the number of pixel values that the display 12 can uniquely present.

The computing device 20, such as the processing circuitry 22, the processor 24 or the like, may also be configured to determine whether there is a lack of perceptible distinctiveness between pixels based upon a luminance range of the display 12 and just noticeable indices. By way of example in which pixel values of the input image within a window having a range ($W_{left}$, $W_{right}$) are transformed to presentation pixel values of the range ($P_{min}$, $P_{max}$), the computing device, such as the processing circuitry, the processor or the like, may be configured to initially retrieve the luminance range supported by the display, such as from the display, from a value stored by memory 26 or the like. The luminance range supported by the display is denoted ($Lum_{min}$, $Lum_{max}$). The computing device, such as the processing circuitry, the processor or the like, may be configured to determine the just noticeable difference (JND) index for $Lum_{min}$ and $Lum_{max}$ by substituting these values for L in the following equation:

$$JND(L)=A+B\ Log_{10}(L)+C(Log_{10}(L))^2+D(Log_{10}(L))^3+E(Log_{10}(L))^4+F(Log_{10}(L))^5+G(Log_{10}(L))^6+H(Log_{10}(L))^7+I(Log_{10}(L))^8 \quad \text{Equation (1)}$$

In the foregoing Equation 1, $Log_{10}$ represents a log logarithm to the base 10 and the constants A-I may be predefined as follows: A=71.498068, B=94.593053, C=41.912053, D=9.8247004, E=0.28175407, F=−1.1878455, G=−0.18014349, H=0.14710899 and I=−0.017046845. As set forth by Equation 1, the computing device 20, such as the processing circuitry 22, the processor 24 or the like, may be configured to determine discrete JND indexes for the modality luminance range ($Lum_{min}$, $Lum_{max}$) as $j_{min}$=JND ($Lum_{min}$) and $j_{max}$=JND ($Lum_{max}$). In this regard, the span of JND index values may range from $j_{min}$ for a presentation pixel value of $P_{min}$ to $j_{max}$ for a presentation pixel value of $P_{max}$ with the JND index values defined as follows:

$$JND(P_{value}) = j_{min} + \frac{(j_{max} - j_{min})}{P_{max} - P_{min}} * P_{value} \quad \text{Equation (2)}$$

It is noted that the foregoing Equation 2 represents a linear line having a slope equal to:

$$\text{Slope} = \frac{j_{max} - j_{min}}{P_{max} - P_{min}} \quad \text{Equation (3)}$$

The JND index values are integer values such that when the slope is less than 1, two or more consecutive presentation pixel values within the range ($P_{min}$, $P_{max}$) may be mapped to the same JND index value and therefore not be perceptually distinguishable. Thus, the computing device 20, such as the processing circuitry 22, the processor 24 or the like, may be configured to determine that there is a lack of perceptible distinctiveness between pixels within the window in an instance in which the slope of the JND index function is less than 1.

As shown in FIG. 6, the computing device 20, such as the processing circuitry 22, the processor 24 or the like, may be configured to determine if a pixel loss condition exists, as shown at block 44. If a pixel loss condition does not exist, the process may end. However, in an instance in which a pixel visibility loss condition does exist, the computing device, such as the processing circuitry, the processor or the like, may be configured to cause an indication to be provided to a user. See block 46 of FIG. 6. For example, a visible indication may be provided via the display 12, such as a presentation of light icon, a message, e.g., a warning, a flashing light or some other visible indication, such as the blinking of a cursor. In an example embodiment, the visible indication may also provide information regarding the extent of the pixel visibility loss condition, such as the number of pixel values of the input image that are not uniquely and distinctly represented by the image presented by the display, such as by causing a visible indication to be provided that has an intensity that corresponds, e.g., is proportional, to the extent of the pixel visibility loss condition. Additionally or alternatively, other types of indications may be provided, such as an audible indication or the like. As such, the computing device of an example embodiment may alert the user that not all input pixel values are uniquely represented by the image presented by the display. Based upon the indication that a pixel visibility loss condition exists, the user may take the pixel visibility loss condition into account in their analysis of the image. Additionally or alternatively, the user may modify the window and level values and/or the corresponding minimum and maximum values for the window in order to eliminate the pixel visibility loss condition or to view other input pixel values.

By way of example in which the window has a width W and a level L and maximum and minimum values of $W_{left}$ and $W_{right}$, respectively, an input image having minimum and maximum input pixel values of $X_{min}$ and $X_{max}$ may be analyzed by the computing device 20, such as the processing circuitry 22, the processor 24 or the like, to determine whether there is a grayscale loss, e.g., GrayScaleLoss, as follows:

$W_{left}$ = L −0.5 − (W−1)/2;
$W_{right}$ = L −0.5 + (W−1)/2;

-continued

```
if ( (W_left < X_min) OR (W_right > X_max) )
    GrayScaleLoss = TRUE ;
else
    GrayScaleLoss= False.
```

Continuing with this example, the computing device 20, such as the processing circuitry 22, the processor 24 or the like, may be configured to determine whether there is a grayscale compression, e.g., GrayScaleCompression, for consecutive pixel values in an instance in which the pixel presentation value range is $2^n$ with n being the number of bits supported by the display 12 as follows:

```
W_left = L -0.5 - (W-1)/2;
W_right = L -0.5 + (W-1)/2;
if ((W_left >= X_min) AND (W_right <= X_max)
    if ( W > 2n)
        i= W_left;
        for all i of the range (W_left , W_right)
            if (h(i)> 0 AND h(i+1) >0)
                GrayScaleCompression = True;
    else
        GrayScaleCompression = False.
```

Still further, the computing device 20, such as the processing circuitry 22, the processor 24 or the like, of this example embodiment may be configured to determine whether there is a lack of perceptible distinctiveness in an instance in which pixels within a window having a range of ($W_{left}$, $W_{right}$) are transformed to presentation pixel values in the range ($P_{min}$, $P_{max}$) by determining whether the presentation pixel value range is perceptually distinguishable as follows:

1. Retrieve the supported luminance range ($Lum_{Min}$, $Lum_{Max}$) of the display 12
2. Determine $j_{min}$, that is, the Just Noticible Difference (JND) index for $Lum_{Min}$
3. Determine $j_{max}$, that is, the Just Noticible Difference (JND) index for $Lum_{Max}$
4. Calculate the value of a slope defined by $(j_{max} - j_{min})/(P_{min} - P_{max})$
5. if (slope ≥1)
   WindowPixelRangePerceptualyDifferent = True;
   else
   WindowPixelRangePerceptualyDifferent = False.

The computing device 20, such as the processing circuitry 22, the processor 24 or the like, may be configured to determine whether a pixel visibility loss condition exists at the time that an image is initially displayed. Thereafter, as the window is moved within the same image or as another input image is presented, the computing device may be configured to again determine whether a pixel visibility loss condition exists based upon the current configuration of the window and the input mage to be presented, thereby providing an updated indication to the user as to whether there is a pixel visibility loss condition.

In another example embodiment depicted in FIG. 7, the computing device 20, such as the processing circuitry 22, the processor 24 or the like, may be configured to identify each distinct pixel value of the input image, as shown at block 52. The computing device, such as the processing circuitry, the processor or the like, may also be configured to associate a respective pixel visibility flag, such as may be maintained by memory 26, with each distinct pixel value. See block 54. As shown in block 56 of FIG. 7, the computing device, such as the processing circuitry, the processor or the like, may be configured to determine whether there is grayscale loss, grayscale compression or a perceptible distinctiveness between pixels within the window. In an instance in which the computing device, such as the processing circuitry, the processor or the like, determines that there is grayscale loss, grayscale compression and/or a lack of perceptible distinctiveness between pixels within the image, the pixel visibility flag associated with each pixel value within the window may be set as shown in block 58. In accordance with this embodiment, the computing device, such as the processing circuitry, the processor or the like, may be configured to determine whether all pixel visibility flags for the pixel values of the input image have been set. See block 60. If not, the computing device, such as the processing circuitry, the processor or the like, may be configured to cause an indication to be provided, such as a visible indication. See block 62 of FIG. 7. However, in an instance in which the computing device, such as the processing circuitry, the processor or the like, determines that the pixel visibility flags for the pixel values of the input image have not all been set, no indication need be provided.

In one example embodiment, the computing device 20, such as the processing circuitry 22, the processor 24 or the like, may be configured to initially cause a visible indication to be provided as shown in block 50. In an instance in which it is determined that all pixel visibility flags for the pixel values of the input image have not been set, the visible indication may be eliminated as shown in block 64. Conversely, the visible indication may be maintained in an instance in which all pixel visibility flags for the pixel values of the input image have been set. See block 62.

The computing device 20, as well as the corresponding method and computer program product, are therefore configured to identify an instance in which a pixel visibility loss condition exists following window leveling. Based upon the identification of a pixel visibility loss condition, the method, computing device and a computer program product may notify a user so that the user is put on notice that the input image has been modified and that not all pixel values of the input image are uniquely and distinctly represented by the image presented by the display 12. As such, a user can take into account the modification of the input image in analyzing the image that is presented by the display.

As described above, FIGS. 6 and 7 are flowcharts of a method, computing device 20 and computer program product according to example embodiments of the invention. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 26 of a computing device and executed by processing circuitry 22 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowcharts support combinations of means for performing the specified functions and combinations of steps for performing the specified functions. It will also be understood that one or more blocks of the flowcharts, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 22 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:
1. A method comprising:
for a window defining a range of pixel values that are capable of being simultaneously presented by a display, identifying window and level values and corresponding minimum and maximum values for a window, wherein the level value corresponds to a center of the range of pixel values that define the window;
determining, with processing circuitry, whether a pixel visibility loss condition exists based upon one or more of the window and level values, the minimum value or the maximum value, wherein determining whether a pixel visibility loss condition exists comprises determining whether there is a lack of perceptible distinctiveness between pixels within the window based on a luminance range of the display and just noticeable indices, wherein determining whether there is a lack of perceptible distinctiveness between pixels within the window comprises determining that there is a lack of perceptible distinctiveness between pixels within the window in that two or more consecutive presentation pixel values may be mapped to a same just noticeable index in an instance in which a ratio of: (i) a difference between first and second just noticeable indices for first and second luminance values, respectively, to (ii) a difference between the first and second presentation pixel values corresponding both to the first and second just noticeable indices, respectively, and to transformed representations of first and second pixel values, respectively, is less than one; and
in an instance in which the pixel visibility loss condition exists, causing an indication to be provided to a user.

2. A method according to claim 1 wherein determining whether a pixel visibility loss condition exists comprises determining whether there is a gray scale loss which one or more gray scale values in an input image are not assigned to any pixel value to be presented by a display.

3. A method according to claim 1 wherein determining whether a pixel visibility loss condition exists comprises determining whether there is a gray scale compression in which a single display value to be presented by a display is assigned to two or more pixel values within the window.

4. A method according to claim 1 wherein the first and second luminance values are maximum and minimum luminance values, respectively, supported by the display.

5. A method according to claim 1 wherein causing an indication to be provided to a user comprises causing a visible indication to be provided via the display.

6. A computing device comprising processing circuitry configured to:
for a window defining a range of pixel values that are capable of being simultaneously presented by a display, identify window and level values and corresponding minimum and maximum values for a window, wherein the level value corresponds to a center of the range of pixel values that define the window;
determine whether a pixel visibility loss condition exists based upon one or more of the window and level values, the minimum value or the maximum value by determining whether a pixel visibility loss condition exists comprises determining whether there is a lack of perceptible distinctiveness between pixels within the window based on a luminance range of the display and just noticeable indices, wherein determining whether there is a lack of perceptible distinctiveness between pixels within the window comprises determining that there is a lack of perceptible distinctiveness between pixels within the window in that two or more consecutive presentation pixel values may be mapped to a same just noticeable index in an instance in which a ratio of: (i) a difference between first and second just noticeable indices for first and second luminance values, respectively, to (ii) a difference between the first and second presentation pixel values corresponding both to the first and second just noticeable indices, respectively, and to transformed representations of first and second pixel values, respectively, is less than one; and in an instance in which the pixel visibility loss condition exists, cause an indication to be provided to a user.

7. A computing device according to claim 6 wherein the processing circuitry is configured to determine whether a pixel visibility loss condition exists by determining whether there is a gray scale loss in which one or more gray scale values in an input image are not assigned to any pixel value to be presented by a display.

8. A computing device according to claim 6 wherein the processing circuitry is configured to determine whether a pixel visibility loss condition exists by determining whether there is a gray scale compression in which a single display value to be presented by a display is assigned to two or more pixel values within the window.

9. A computing device according to claim 6 wherein the first and second luminance values are maximum and minimum luminance values, respectively, supported by the display.

10. A computing device according to claim 6 wherein the processing circuitry is configured to cause an indication to be provided to a user by causing a visible indication to be provided via the display.

11. A method comprising:
identifying each distinct pixel value of an input image;
associating a respective pixel visibility flag with each distinct pixel value;
for a window defining a range of pixel values that are capable of being simultaneously presented by a display and a level corresponding to a center of the range of pixel values that define the window, determining, with processing circuitry, whether there is a lack of perceptible distinctiveness between pixels within the window based upon window and level values and corresponding minimum and maximum values for the window, wherein the lack of perceptible distinctiveness is based on a luminance range of the display and just noticeable indices, and wherein determining whether there is a lack of perceptible distinctiveness between pixels within the window comprises determining that there is a lack of perceptible distinctiveness between pixels within the window in that two or more consecutive presentation pixel values may be mapped to a same just noticeable index in an instance in which a ratio of: (i) a difference between first and second just noticeable indices for first and second luminance values, respectively, to (ii) a difference between the first and second presentation pixel values corresponding both to the first and second just noticeable indices, respectively, and to transformed representations of first and second pixel values, respectively, is less than one;
in an instance in which there is no lack of perceptible distinctiveness between pixels within the window, setting the pixel visibility flag associated with each pixel value within the window; and
in an instance in which not all pixel visibility flags for the pixel values of the input image have been set, causing an indication to be provided to a user.

12. A method according to claim 11 further comprising determining whether there is a gray scale compression in which a single display value to be presented by a display is assigned to two or more pixel values within the window.

13. A method according to claim 11 wherein the first and second luminance values are maximum and minimum luminance values, respectively, supported by the display.

14. A method according to claim 11 wherein causing an indication to be provided to a user comprises causing a visible indication to be provided via the display.

15. A method according to claim 14 further comprising initially causing the visible indication to be provided prior to determining whether there is a lack of perceptible distinctiveness between pixels within the window, wherein causing the visible indication to be provided to the user comprises eliminating the visible indication in the instance in which all pixel visibility flags for the pixel values of the input image have been set.

16. A computing device comprising processing circuitry configured to:
identify each distinct pixel value of an input image;
associate a respective pixel visibility flag with each distinct pixel value;
for a window defining a range of pixel values that are capable of being simultaneously presented by a display and a level corresponding to a center of the range of pixel values that define the window, determine whether there is a lack of perceptible distinctiveness between pixels within the window based upon window and level values and corresponding minimum and maximum values for the window, wherein the lack of perceptible distinctiveness is based on a luminance range of the display and just noticeable indices, and wherein the processing circuitry is configured to determine whether there is a lack of perceptible distinctiveness between pixels within the window comprises determining that there is a lack of perceptible distinctiveness between pixels within the window in an instance in which a ratio of: (i) a difference between first and second just noticeable indices for first and second luminance values respectively, to (ii) a difference between the first and second presentation pixel values corresponding both to the first and second just noticeable indices, respectively, and to transformed representations of first and second pixel values, respectively, is less than one;
in an instance in which there is no lack of perceptible distinctiveness between pixels within the window, set the pixel visibility flag associated with each pixel value within the window; and
in an instance in which not all pixel visibility flags for the pixel values of the input image have been set, cause an indication to be provided to a user.

17. A computing device according to claim 16 wherein the processing circuitry is further configured to determine whether there is a gray scale compression in which a single display value to be presented by a display is assigned to two or more pixel values within the window.

18. A computing device according to claim 16 wherein the first and second luminance values are maximum and minimum luminance values, respectively, supported by the display.

19. A computing device according to claim 16 wherein the processing circuitry is configured to cause an indication to be provided to a user by causing a visible indication to be provided via the display.

20. A computing device according to claim 19 wherein the processing circuitry is further configured to initially cause the visible indication to be provided prior to determining whether there is a lack of perceptible distinctiveness between pixels within the window, wherein the processing circuitry is configured to cause the visible indication to be provided to the user by eliminating the visible indication in the instance in which all pixel visibility flags for the pixel values of the input image have been set.

* * * * *